United States Patent
Lindsey et al.

(10) Patent No.: US 12,419,612 B2
(45) Date of Patent: Sep. 23, 2025

(54) PREOPERATIVE METHOD AND SYSTEM FOR MINIMIZING WOUND COMPLICATIONS

(71) Applicants: John T. Lindsey, New Orleans, LA (US); Chris Spring, New Orleans, LA (US)

(72) Inventors: John T. Lindsey, New Orleans, LA (US); Chris Spring, New Orleans, LA (US)

( * ) Notice: Subject to any disclaimer, the term of this patent is extended or adjusted under 35 U.S.C. 154(b) by 0 days.

(21) Appl. No.: 18/198,697

(22) Filed: May 17, 2023

(65) Prior Publication Data

US 2024/0090874 A1    Mar. 21, 2024

Related U.S. Application Data

(60) Provisional application No. 63/407,939, filed on Sep. 19, 2022.

(51) Int. Cl.
| | |
|---|---|
| *A61B 8/00* | (2006.01) |
| *A61B 8/08* | (2006.01) |
| *G06N 3/08* | (2023.01) |
| *G06T 7/00* | (2017.01) |

(52) U.S. Cl.
CPC ............ *A61B 8/469* (2013.01); *A61B 8/0858* (2013.01); *G06N 3/08* (2013.01); *G06T 7/0012* (2013.01); *G06T 2207/10132* (2013.01)

(58) Field of Classification Search
None
See application file for complete search history.

(56) References Cited

U.S. PATENT DOCUMENTS

| | | | |
|---|---|---|---|
| 2022/0062660 A1* | 3/2022 | Verner Rashkovsky | ................... A61N 7/00 |
| 2023/0225670 A1* | 7/2023 | Sasaki | ..................... A61B 8/00 600/546 |

OTHER PUBLICATIONS

Straughan et al., "Preoperative Evaluation of the Superficial Fascial System Can Predict Wound Complications in Body Contouring Surgery," (June 202), Ann Plast Surg 2020;84: S401-S404. (Year: 2020).*

(Continued)

*Primary Examiner* — Keith M Raymond
*Assistant Examiner* — Ashish S Jasani
(74) *Attorney, Agent, or Firm* — Intellectual Property Consulting, LLC; Stephen M. Kepper

(57) ABSTRACT

A system and method for preoperatively predicting wound complications and recommending tension reducing procedures is disclosed. The system includes (i) ultrasound imaging technology operable to take an ultrasound of a portion of subcutaneous tissue on a patient, (ii) image processing and filtering technology operable to focus on a portion of the tissue and filter out the overlying dermis, underlying muscle, and muscle fascia, and (iii) processing means capable of determining the Mean Gray Value (MGV) from the imaged sample. The method further includes tension reducing procedures for patients with a MGV less than 0.127 to minimize foreseeable wound complications. The system may include a processor and image classification engine operable to classify any ultrasound image and determine the MGV from the imaged sample.

6 Claims, 9 Drawing Sheets

(56) References Cited

OTHER PUBLICATIONS

Guidry et al., "Ultrasound Imaging of the Superficial Fascial System Can Predict the Subcutaneous Strength of Abdominal Tissue Using Mean Gray Value Quantification," (May 2020), Plastic and Reconstructive Surgery 145(5):p. 1173-1181. (Year: 2020).*

Mcquin et al., "CellProfiler 3.0: Next-generation image processing for biology," (Jul. 3, 2018), PLoS Biol 16(7): e2005970. (Year: 2018).*

* cited by examiner

FIG. 6A
FIG. 6B
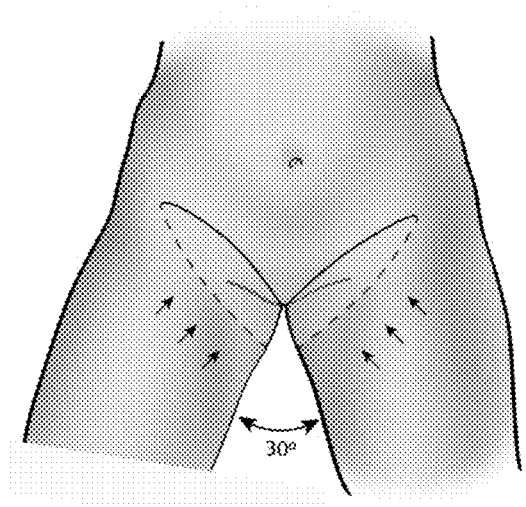
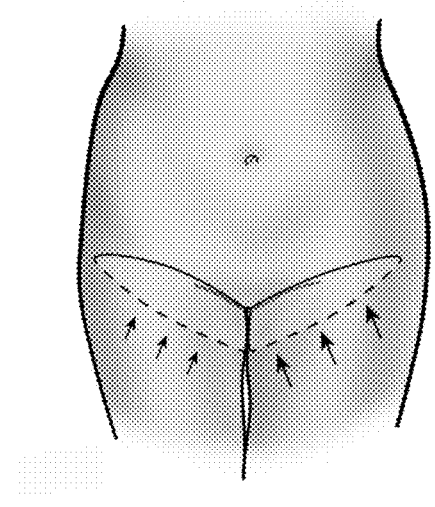

PREOPERATIVE METHOD AND SYSTEM FOR MINIMIZING WOUND COMPLICATIONS

RELATED APPLICATIONS

This application claims priority to U.S. Provisional Application No. 63/407,939 filed Sep. 19, 2022. The entire contents of the above applications are hereby incorporated by reference as though fully set forth herein.

FIELD OF TECHNOLOGY

The present invention relates in general to preoperative medical procedures, and in particular to a system and method for minimizing wound complications during surgery.

BACKGROUND

Dramatic weight loss has many benefits. But after any substantial amount of weight loss due to weight loss surgery and/or lifestyle changes, the skin and tissues often lack the elasticity to conform to the reduced body size. Surgical body contouring following major weight loss, pregnancy, or because of the normal ageing process, removes excess sagging skin and fat while restoring or improving the shape of the body. The result is a better-proportioned appearance, smoother contours, and often improved functionality. As a result, the demand for body contouring surgery continues to rise.

One increasingly popular procedure that enhances the functional and aesthetic outcomes in this population is that of abdominoplasty. According to the American Society of Plastic Surgeons, the number of abdominoplasties has risen 107 percent since 2000, up to 130,081 procedures in the United States in 2018. Other body contouring procedures such as brachioplasty and thighplasty have likewise increased in the United States and worldwide in a similar fashion. Although popularity of plastic surgery is on the rise, wound complications reported as high as 51.8 percent in bariatric patients have plagued these procedures.

With these procedures in high demand, there is a need to address the high percentage of wound complications associated with these procedures.

BRIEF SUMMARY OF THE INVENTION

In a first embodiment, a system and method for predicting wound complications is disclosed. The system includes (i) ultrasound imaging technology operable to take an ultrasound of a portion of subcutaneous tissue on a patient, (ii) image processing and filtering technology operable to focus on a portion of the tissue and filter out the overlying dermis, underlying muscle, and muscle fascia, and (iii) processing means capable of determining the Mean Gray Value (MGV) from the imaged sample. Based on the MGV value, a reliable prediction of wound complications can be provided to the patient as well as recommendations for tension-reducing procedures to minimize foreseeable wound complications. Such procedures involve skin excision and advancement, while ensuring appropriate and consistent patient positioning and avoidance of wound tension and skin pleating in at-risk patients.

In a second embodiment, the system comprises a processing module including a processor and image classification engine having a neural network trained to classify any ultrasound image into the following sets of data labels: (i) type of ultrasound image, (ii) size of the ultrasound image, (iii) size of the target area of interest (i.e. portion of the tissue after filtering out the overlying dermis, underlying muscle, and muscle fascia), and (iv) annotated descriptor for the region of the human body being examined. The processing module is operable to determine the MGV of the target area of interest to predict wound complications.

A third embodiment includes the method for training the neural network comprising the steps of (i) providing a training dataset of ultrasound images to the neural network with labels corresponding to each data label described above, (ii) receiving a predicted output, (iii) adjusting the weights of the neural network to minimize the difference between the predicted output and the actual label of each image in the training dataset, and (iv) repeating the above steps until the neural network can predict the category of new, unseen images with a high degree of accuracy.

BRIEF DESCRIPTION OF THE DRAWINGS

FIG. 6A is a diagram depicting a tension reducing procedure in accordance with embodiments of the invention by showing a thigh lift skin excision planned and measured with thighs in 30 degrees of abduction for patients.

FIG. 6B is a diagram that shows a thigh lift skin excision incorrectly planned and measured with the thighs fully adducted for patients.

DETAILED DESCRIPTION

Figure 1:
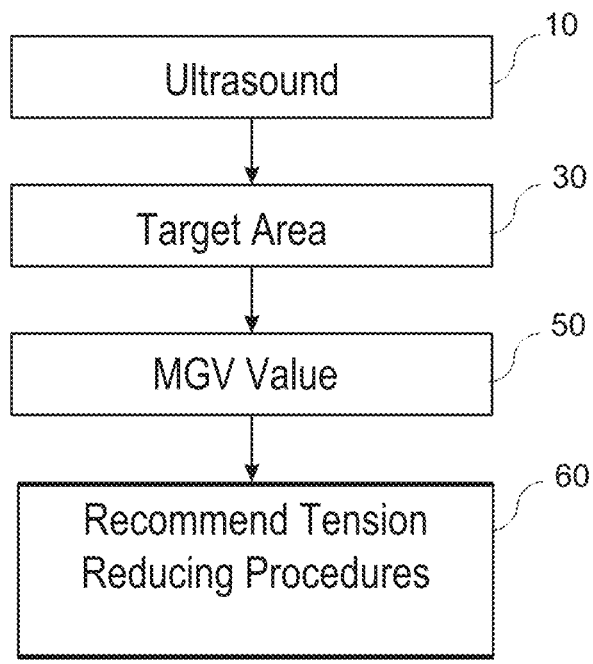
FIG. 1 is a flow diagram showing a method for predicting wound complications preoperatively in accordance with the embodiments of the present invention.

A system and method for preoperatively predicting wound complications for a patient undergoing body contouring surgery is shown in FIG. 1. The first step 10 in the method requires the use of ultrasound imaging technology to take an ultrasound image of the portion of the patient's body where the surgery is to take place. In one embodiment, this step is accomplished using, for example, a Lumify portable ultrasound system which allows the physician to view the subcutaneous tissue. This imaging is preferably accomplished in B mode on a Samsung Galaxy Tab A tablet on the superficial setting, gain set to 54 and depth settings between 2.5-4 cm, depending on the thickness of the subcutaneous tissue. Exemplary ultrasound images 20 taken using the Lumify portable ultrasound system for two separate patients undergoing abdominoplasty are shown in FIGS. 3A and 3B.

Figure 3A:
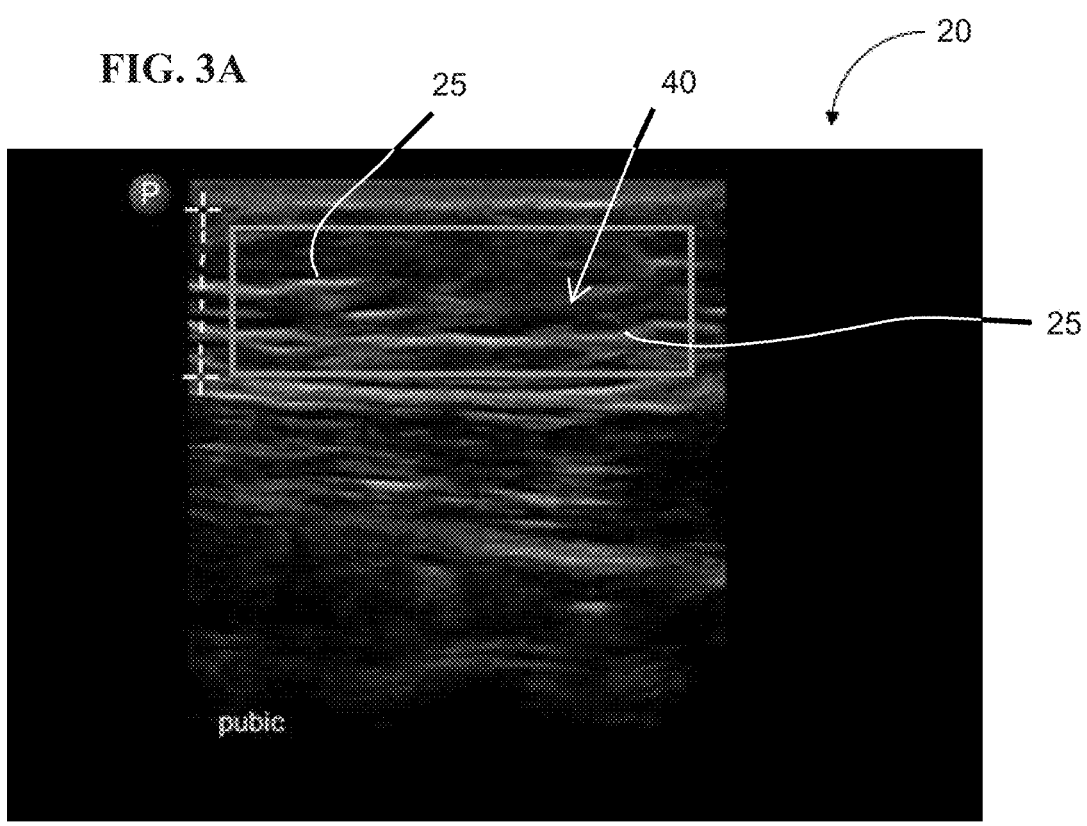
FIG. 3A is an ultrasound image showing the pubic area of the lower anterior abdominal wall in a patient undergoing abdominoplasty. The cropped image, as indicated by the rectangle, excludes the overlying dermis and underlying muscle and muscle fascia.
Figure 3B:
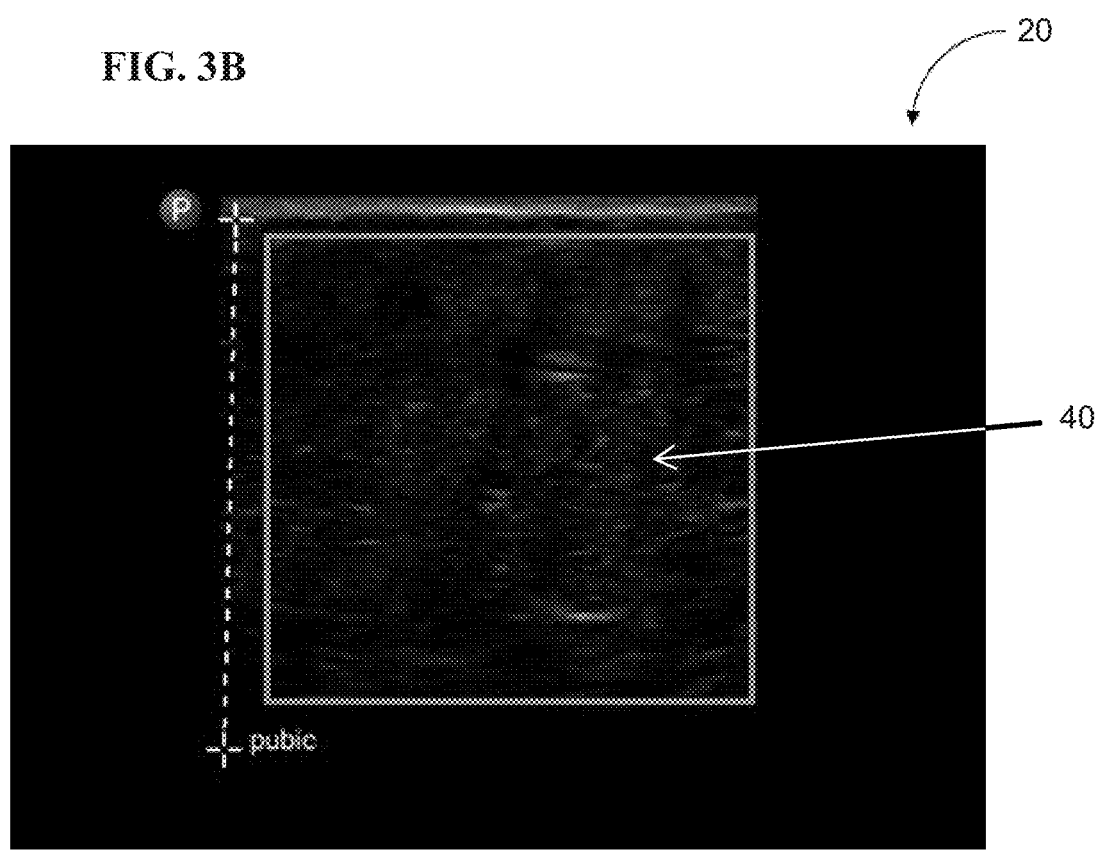
FIG. 3B is an ultrasound image showing the pubic area of the lower anterior wall in a different patient undergoing abdominoplasty. The cropped image, as indicated by the rectangle, excludes the overlying dermis and underlying muscle and muscle fascia.

The second step 30 in the method is to crop the image 20 to focus on the target area 40 (as shown in FIGS. 3A-3B) of the image 20 by excluding the overlying dermis and underlying muscle and muscle fascia. This step is accomplished using, for example, XnView, or any equivalent software. As shown in FIGS. 3A and 3B, the portions of the ultrasound image 20 within the rectangles demonstrate the target areas 40 of subcutaneous tissue cropped by XnView.

The third step 50 in the method includes analyzing the cropped image to determine the MGV of the ultrasound image 20. This step is accomplished using, for example, CellProfiler, or its equivalent, to determine the MGV of the sample based on the following equation:

$$\text{Mean Gravy Value} = \frac{\Sigma \text{ Echogenicity of Each Pixel}}{\text{Number of Pixels in Image}}$$
$$= \frac{\text{Total Echogenicity of Image}}{\text{Area}}$$

As shown in FIG. 3A, the image 20 includes multiple horizontally-oriented streaks of white, reflective collagen 25 that indicate a strong SFS (superficial fascial system) in this area with a corresponding MGV of 0.16296. Conversely, the image depicted in FIG. 3B shows the subcutaneous tissue almost devoid of collagen 25 which indicates a weak SFS with a corresponding MGV of 0.06206.

In the fourth step 60, patients with average to poor MGV (0.127 or less) are identified preoperatively for recommended tension-reducing procedures to reduce wound complications before undergoing a specific type of body contouring procedure. The primary purpose of these tension reducing procedures is to avoid tension of the skin during wound closure, which is a common cause of wound complications. The recommended clinical maneuvers undertaken to reduce tension closure in body contouring surgery are depicted in FIGS. 4, 5B, 6A, and 7A, each of which are summarized below.

Figure 4:
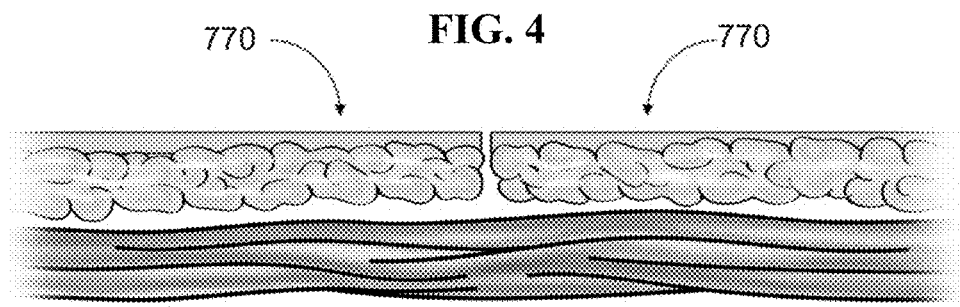
FIG. 4 is a diagram depicting a tension reducing procedure in accordance with embodiments of the invention by showing a cross-section view of human skin with skin flap margins in apposition after measured resection prior to final layered wound closure.

As shown in FIG. 4, each tension reducing procedure involves removing excess skin so that cut skin flaps 70 lay in apposition rather than gap apart. Closing a gap in the skin during body contouring provides improved appearance and contour but at a risk of wound-healing complications. There should be no gap in the skin flaps at closure for patients with MGV <0.127.

Figure 5A:
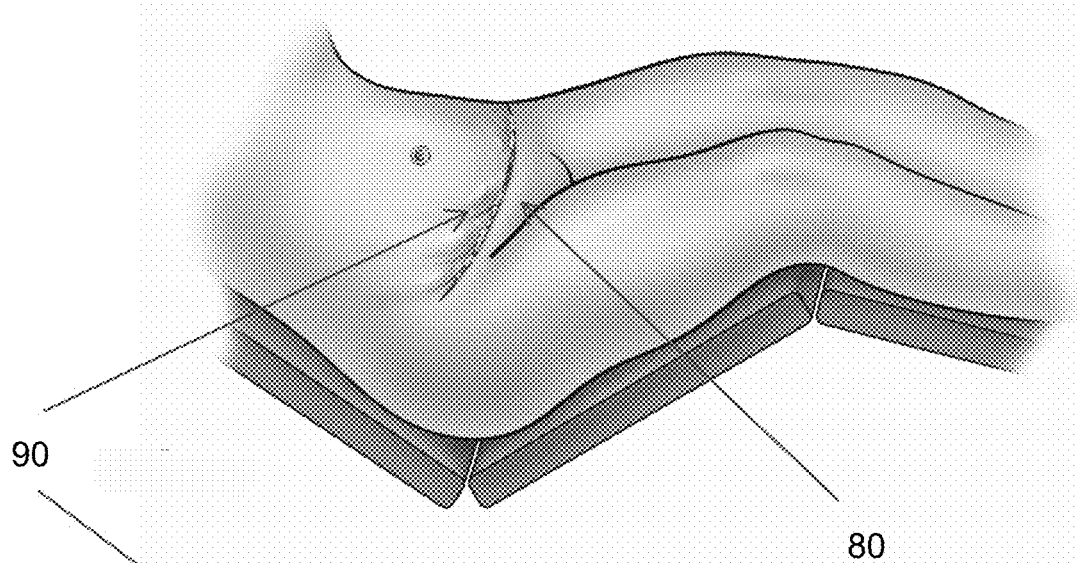
FIG. 5A is a diagram that shows pleating along a lateral abdominoplasty incision.
Figure 5B:
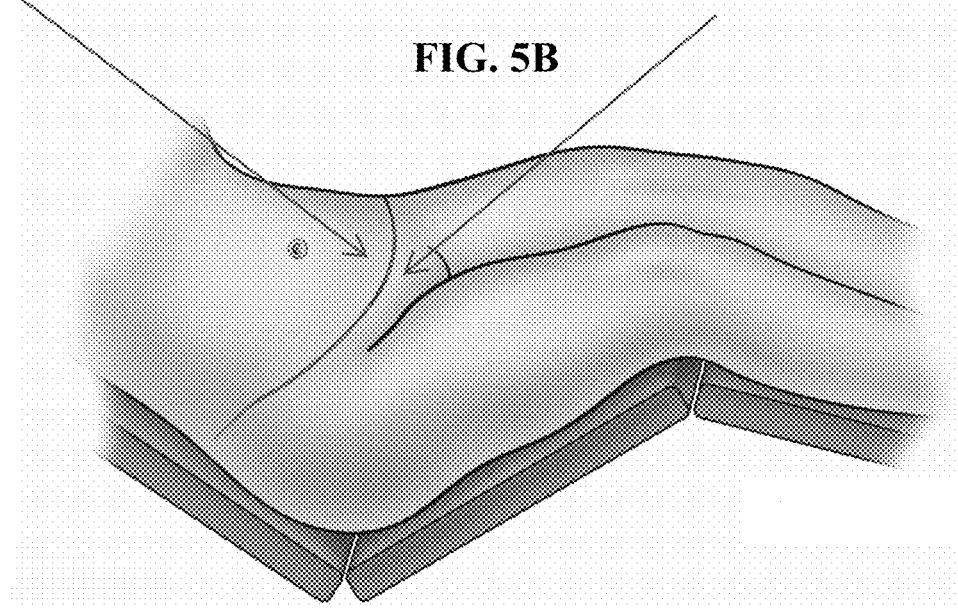
FIG. 5B is a diagram depicting a tension reducing procedure in accordance with embodiments of the invention by showing an incision that has been extended laterally to make-up skin length mismatch and to avoid pleating of the skin.

Another source of wound complications is skin pleating, as there may be irregular and uneven skin margin match at the closure site. This lack of smooth and even skin flap coaptation decreases the wound healing area of contact. The image depicted in FIG. 5A shows post-closure pleating of the skin due to skin length mismatch during an abdominoplasty. This occurs when the length of the more cephalic incision for skin excess is longer than the length of the skin incision for the caudal skin excess. This is a common scenario on many parts of the body where the girth of one body part (i.e., mid-abdominal area) exceeds the girth of another area (hip area), and the intervening skin excess requires removal. In contrast, the image in FIG. 5B avoids skin pleating and demonstrates the recommended tension reducing procedure. As shown, a smooth and uniform wound closure ensues, thus maximizing wound healing contact area of the skin flaps. This is achieved by lengthening the caudal abdominoplasty incision laterally. By doing so, the skin length mismatch between the shorter caudal incision 80 and the longer cephalic incision 90 is averaged over a longer distance, such that pleating of the cephalic skin flap can be progressively diminished until smooth, and maximal soft tissue contact can be achieved during wound closure.

Figure 7A:
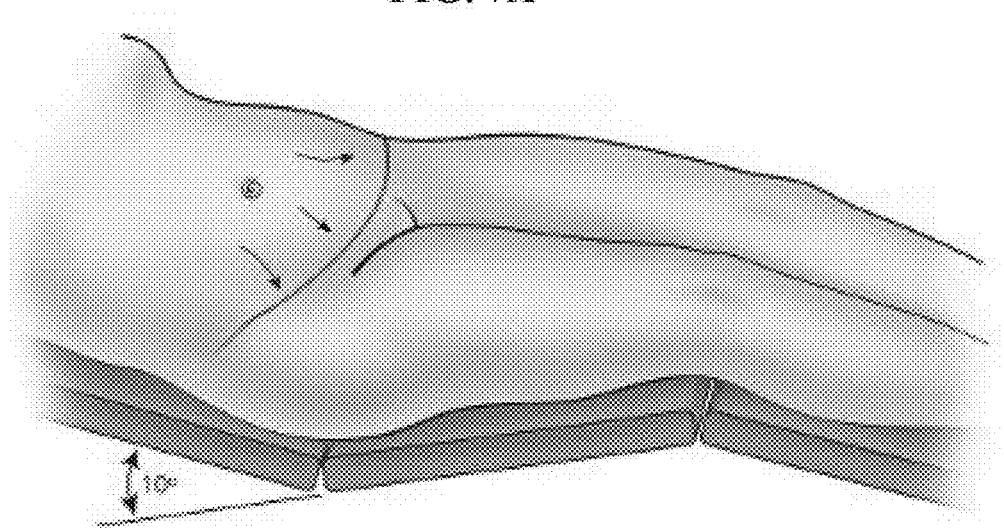
FIG. 7A is a diagram depicting a tension reducing procedure in accordance with embodiments of the invention by showing an abdominoplasty skin excision planned and measured with waist flexed at 10 degrees or less for patients.
Figure 7B:
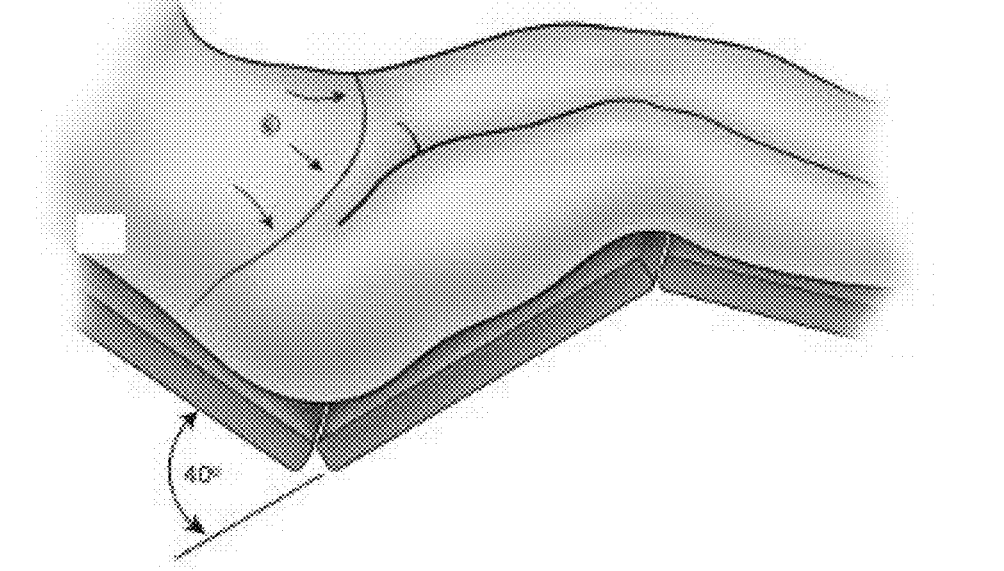
FIG. 7B is a diagram that shows an abdominoplasty skin excision incorrectly planned and measured with typical 40 degree waist flexion for patients.

The other tension reducing procedure includes the avoidance of postural body changes. For patients undergoing the body contouring procedure of a thigh lift closure, for example, the recommended tension reducing procedure for at-risk patients with MGV <0.127 includes skin resection done with skin apposition at 30 degrees of thigh abduction (FIG. 6A) rather than with the thighs fully adducted (FIG. 6B)—the latter of which results in increased tightening and tension and should be done for patients with MGV>0.127. For patients undergoing abdominoplasty with an MGV <0.127, the recommended tension-reducing procedure includes waist flexion limited to no more than 10 degrees as part of "beach chair" positioning, as shown in FIG. 7A. For patients with MGV>0.127, waist flexion as much as 40 degrees (FIG. 7B) is routine. Avoidance of body postural changes for patients with MGV <0.127 decreases wound healing complications.

A study has demonstrated that this method has proven successful in reducing wound complications when compared to a retrospective cohort. As shown in the table below, the cohorts were similar except for a higher incidence of diabetes in the retrospective group (1 v 9, p=0.026, table 1).

|  | Prospective | Retrospective | p-value |
|---|---|---|---|
| Age (yrs) | 45.9 | 47.6 | 0.313 |
| BMI | 29.2 | 28.1 | 0.083 |
| Weight Resected (gr) | 1045.6 | 1180.4 | 0.450 |
| Diabetes | 1 | 9 | 0.026 |
| Smoking | 1 | 0 | — |
| Hx Massive Weight Loss | 4 | 8 | 0.254 |
| Hx Bariatric Surgery | 23 | 30 | 0.323 |
| Wound Complications | 5 | 19 | 0.006 |
| Major Wound Complications | 0 | 1 | 0.978 |
| Total Patients | 112 | 115 |  |

The wound complication rate was significantly reduced in the prospective group (5/112, 4.4%) when compared to the retrospective group (20/115, 17%, p=0.0062).

Figure 8:
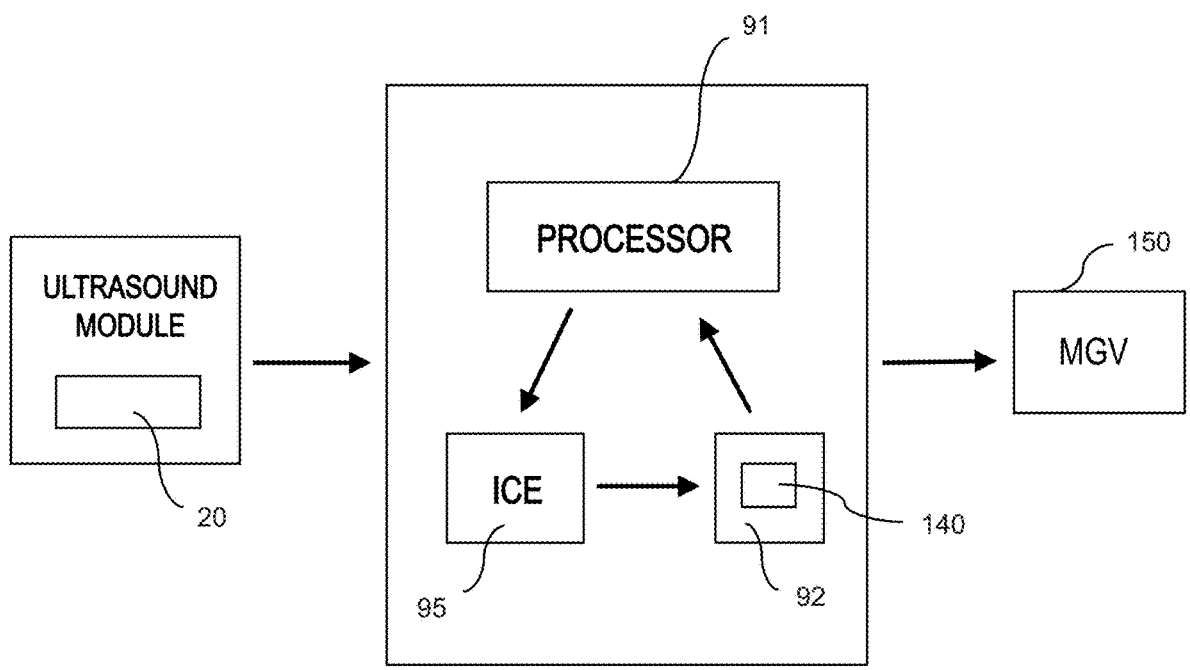
FIG. 8 is a flow diagram showing a system for predicting wound complications preoperatively in accordance with the embodiments of the present invention.
Figure 9:
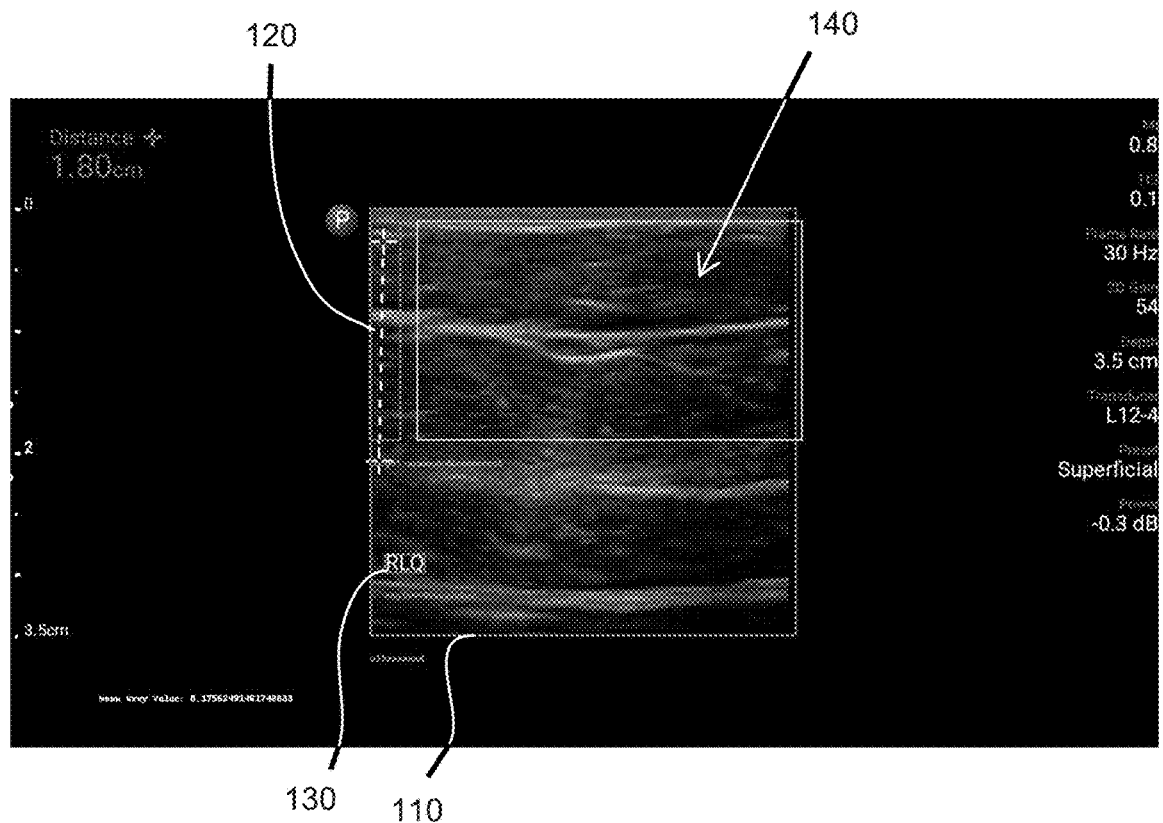
FIG. 9 is an ultrasound image used for the image classification engine in accordance with embodiments of the present invention.
Figure 10:
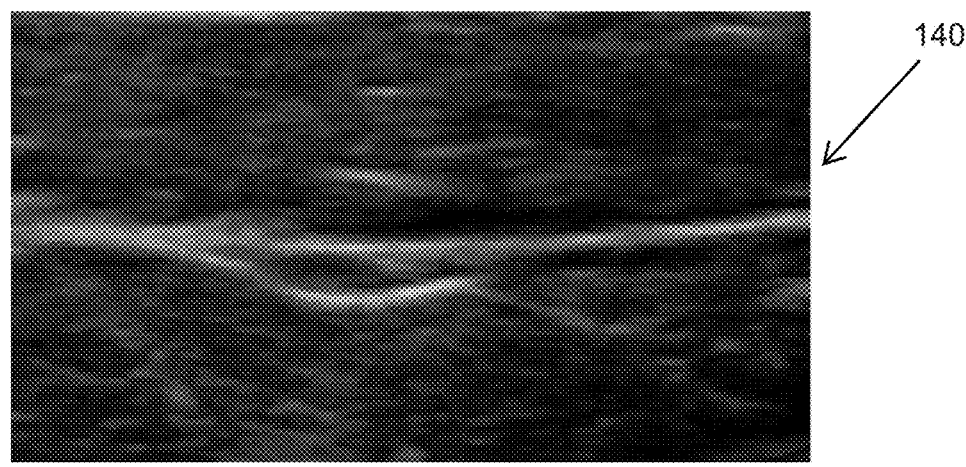
FIG. 10 is a cropped view of a portion of the ultrasound image depicted in FIG. 9 showing the target area of interest.

Turning to FIG. 8, an alternative embodiment of the invention includes a processing module 90 operable to receive an ultrasound image 20 from an ultrasonic machine. The processing module 90 includes a processor 91 and an image classification engine 95 that utilizes a neural network specifically trained to receive an ultrasound image 20 and apply the following labels of data within the ultrasound image 20: (i) type of ultrasound image 100 (not shown), (ii) size of the ultrasound image 110, (iii) size of the target area of interest (i.e. portion of the tissue and filter out the overlying dermis, underlying muscle, and muscle fascia) 120, and (iv) annotated descriptor for the region of the human body being examined 130. An example of the ultrasound image 20 with these labels is show in FIG. 9. The processing module 90 extracts an annotated export image 92 identifying the target area of interest 140 in the image 20 and the associated pixel values. Based on these outputs of data, the processing module 90 can determine the MGV 150 for the target area of interest 140 (as shown in FIG. 10).

Figure 2:
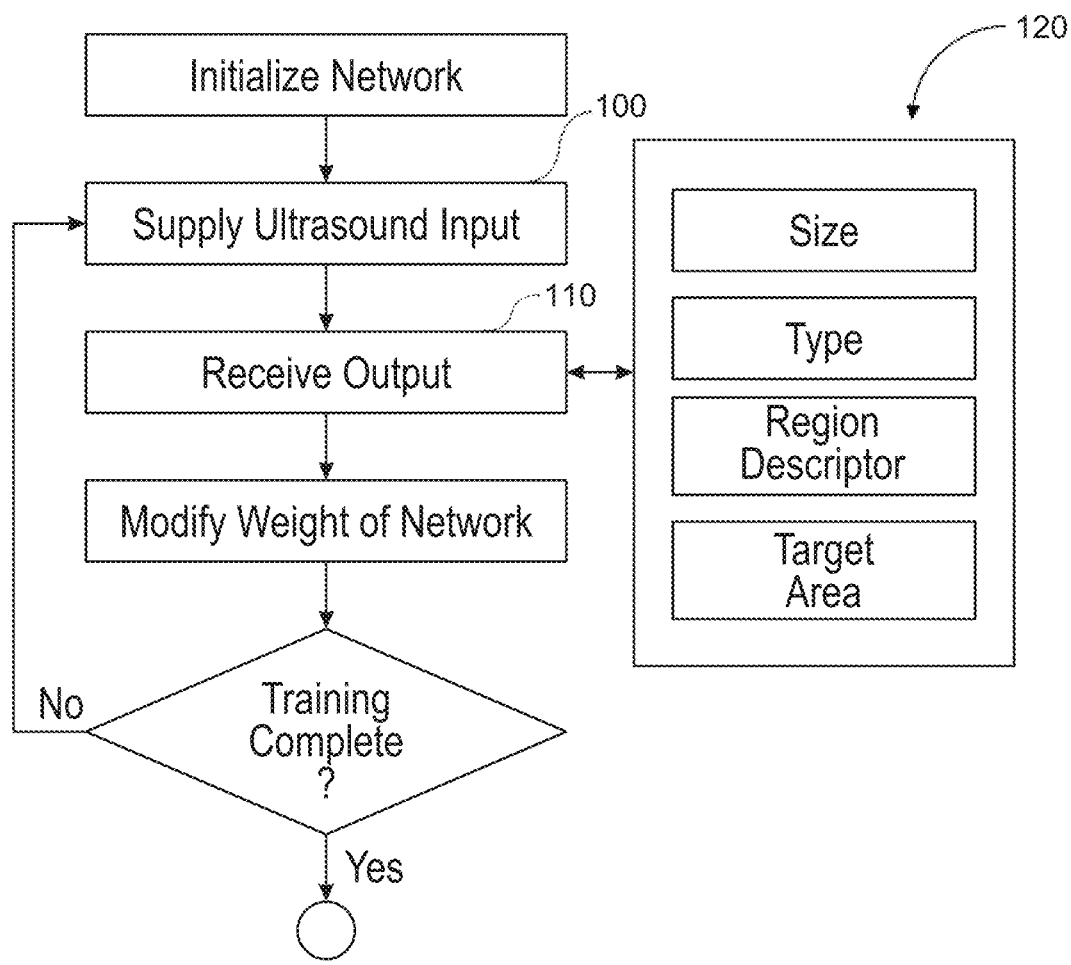
FIG. 2 is a flow diagram showing a method for training a neural network in accordance with the embodiments of the present invention.

Turning to FIG. 2, the method utilized to train the neural network of the image classification engine 95 is disclosed. The neural network is trained on an input dataset of ultrasound images 100 that have been labeled as follows: (i) type of ultrasound image, (ii) size of the ultrasound image, (iii) size of the target area of interest (i.e. portion of the tissue and filter out the overlying dermis, underlying muscle, and muscle fascia), and (iv) annotated descriptor for the region of the human body being examined. The neural network provides a predicted output 110 with its own corresponding labels 120. The weights of the neural network are adjusted to minimize the difference between the predicted output 110 and the actual label of each image in the training dataset 100. These steps are repeated until the neural network can predict each label of new, unseen images with a high degree of accuracy.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method for reducing wound complications for a patient undergoing a thigh lift closure, said method comprising:
    collecting an ultrasound image of a portion of subcutaneous tissue of a patient undergoing a surgical procedure;
    identifying a target area of the subcutaneous tissue, said target area being defined as a portion of said ultrasound that excludes portions of the ultrasound image pertaining to the overlying dermis, underlying muscle, and muscle fascia;
    determining a mean gray value for the target area; and
    if the mean gray value is less than 0.127, recommending skin resection with skin apposition at approximately 30 degrees of thigh abduction.

2. The method of claim 1 further comprising the step of removing excess skin at the wound closure site such that opposing skin flaps lay in apposition prior to final closure.

3. The method of claim 1 further comprising the step of lengthening the shorter, cephalic incision at the wound site to match the length of the longer caudal incision prior to final closure.

4. A method for reducing wound complications for a patient undergoing an abdominoplasty, said method comprising:
    collecting an ultrasound image of a portion of subcutaneous tissue of a patient undergoing a surgical procedure;
    identifying a target area of the subcutaneous tissue, said target area being defined as a portion of said ultrasound that excludes portions of the ultrasound image pertaining to the overlying dermis, underlying muscle, and muscle fascia;
    determining a mean gray value for the target area; and
    if the mean gray value is less than 0.127, recommending waist flexion less than ten degrees.

5. The method of claim 4 further comprising the step of removing excess skin at the wound closure site such that opposing skin flaps lay in apposition prior to final closure.

6. The method of claim 4 further comprising the step of lengthening the shorter,
    caudal incision at the wound site to match the length of the longer cephalic incision prior to final closure.

* * * * *